United States Patent
Pfeiffer et al.

(10) Patent No.: US 10,905,437 B2
(45) Date of Patent: Feb. 2, 2021

(54) DEVICE AND METHOD FOR ALLOGRAFTING

(71) Applicant: THE CURATORS OF THE UNIVERSITY OF MISSOURI, Columbia, MO (US)

(72) Inventors: Ferris M. Pfeiffer, Columbia, MO (US); James L. Cook, Columbia, MO (US); James P. Stannard, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 982 days.

(21) Appl. No.: 15/124,647

(22) PCT Filed: Mar. 12, 2015

(86) PCT No.: PCT/US2015/020168
§ 371 (c)(1),
(2) Date: Sep. 8, 2016

(87) PCT Pub. No.: WO2015/138718
PCT Pub. Date: Sep. 17, 2015

(65) Prior Publication Data
US 2017/0056023 A1    Mar. 2, 2017

Related U.S. Application Data

(60) Provisional application No. 61/967,257, filed on Mar. 13, 2014.

(51) Int. Cl.
*A61B 17/15* (2006.01)
*A61B 17/56* (2006.01)
*A61F 2/46* (2006.01)

(52) U.S. Cl.
CPC ............ *A61B 17/157* (2013.01); *A61B 17/56* (2013.01); *A61F 2/4644* (2013.01)

(58) Field of Classification Search
CPC ... A61B 17/151; A61B 17/152; A61B 17/154; A61B 17/155; A61B 17/157; A61B 17/158; A61F 2002/4645
See application file for complete search history.

(56) References Cited

U.S. PATENT DOCUMENTS 5,053,037 A    10/1991  Lackey
6,648,894 B2 *  11/2003  Abdelgany ........... A61F 2/4644
                                                606/53

(Continued)

FOREIGN PATENT DOCUMENTS

WO    WO 2013/177389 A1    11/2013
WO    WO 2015/138718 A1     9/2015

OTHER PUBLICATIONS

International Search Report and Written Opinion for PCT/US2015/020168, dated Jun. 16, 2015.

*Primary Examiner* — Anu Ramana
(74) *Attorney, Agent, or Firm* — Dentons US LLP

(57) ABSTRACT

In one embodiment, a cutting guide is disclosed for use in a surgical procedure to removed damaged tissue from a patient and form a recipient site configured and dimensioned to receive a donor graft. The cutting guide includes a first arm that abuts a section of the damaged tissue to be removed, and a second arm including a hole and a slot that receives a cutting implement, the first arm and the slot defining a distance therebetween corresponding to a desired dimension of the recipient site. In another embodiment, a cutting guide is disclosed for use in forming a donor graft from donor tissue. The cutting guide includes a body that receives the donor tissue, and a shaping member that is (Continued)

rotatably secured to the body. The shaping member includes at least one vane that shapes the donor tissue so as to form the donor graft.

9 Claims, 6 Drawing Sheets

(56) References Cited

U.S. PATENT DOCUMENTS

| | | | | |
|---|---|---|---|---|
| 6,676,662 | B1* | 1/2004 | Bagga | A61B 17/15 |
| | | | | 606/87 |
| 6,962,592 | B2* | 11/2005 | Gatturna | A61F 2/4644 |
| | | | | 606/184 |
| 8,486,074 | B2* | 7/2013 | Steiner | A61B 17/1635 |
| | | | | 606/79 |
| 2004/0260301 | A1 | 12/2004 | Lionberger et al. | |
| 2008/0183291 | A1 | 7/2008 | Scheller et al. | |
| 2013/0096680 | A1 | 4/2013 | Ribeiro et al. | |

* cited by examiner

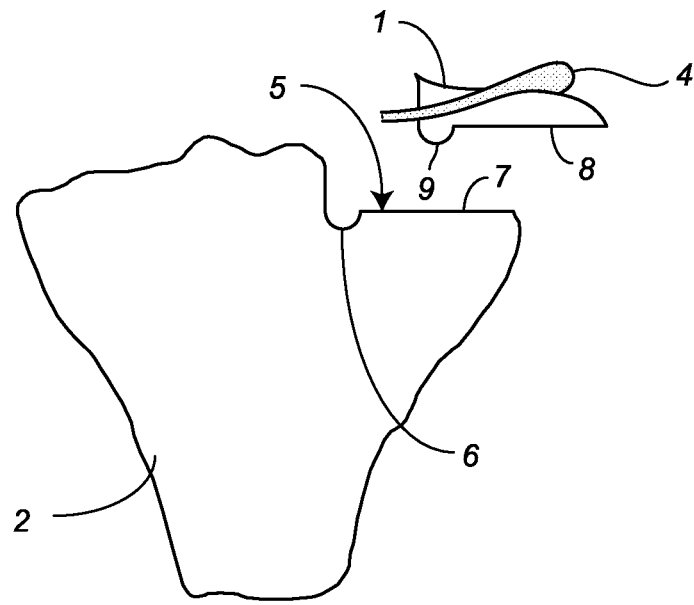
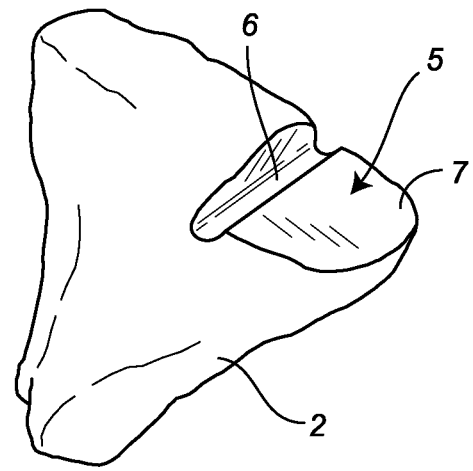
FIG. 3
FIG. 4
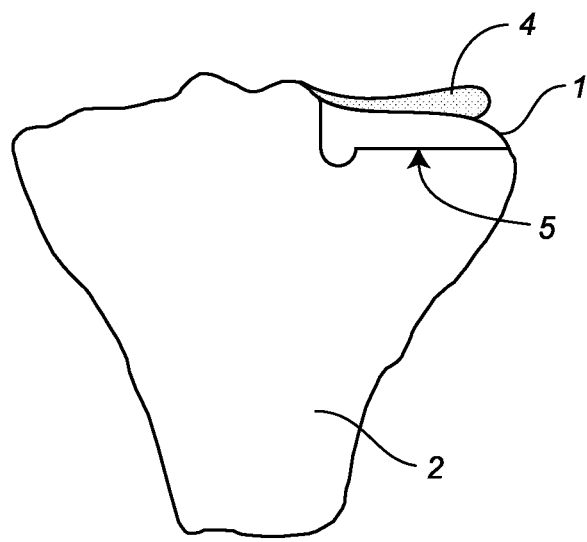
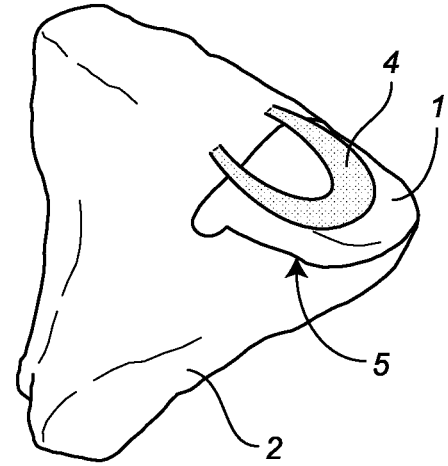
FIG. 5
FIG. 6

DEVICE AND METHOD FOR ALLOGRAFTING

RELATED APPLICATION

This application is a 371 National Stage application of International Application No. PCT/US2015/020168, filed Mar. 12, 2015, which claims the benefit of, and priority to, U.S. Provisional Patent Application Ser. No. 61/967,257, entitled "Device and Method for Tibial Plateau Allografting," filed Mar. 13, 2014, the entire contents of which are hereby incorporated by reference.

BACKGROUND

1. Field

The present disclosure relates to apparatus, systems, and methods for use in tissue grafting procedures, e.g., allografting procedures. For example, the present disclosure relates to apparatus, methods, and systems for use in tibial plateau allografting procedures.

2. Discussion

Few options are available for long term treatment of tibial plateau articular cartilage and/or meniscal injuries, e.g., in young patients, which due to trauma or degeneration, render the joint painful, insufficient, and beyond the ability of native tissue repair techniques. Current standard of care allograft and/or autograft cartilage transplantation techniques are sometimes inappropriate or unable to address tibial plateau cartilage defects, e.g., due to limitations of surgical exposure and current grafting techniques. Additionally, meniscus positioning and attachment to the tibia limits surgical options without disruption of the meniscus. Moreover, during meniscal transplantation, it is often difficult to establish an effective meniscus-bone interface with properties sufficient to withstand physiological loading due to the complex biologic and biomechanical nature of the interface.

As such, a need remains for apparatus, systems, and methods that aid in the graft implantation process, and have sufficient healing and functional performance to be utilized in a wide range of patients with joint pathology.

SUMMARY

In one aspect of the present disclosure, an allograft tibial plateau implant system is described, as well as corresponding methods of use, that utilize a tongue-and-groove interlocking mechanism. More specifically, the disclosed system and methods create and use an allograft tibial plateau implant with a bulging outward-curved ledge (tongue member) that is received by an implant recipient site prepared with a matching inward-curved to groove/channel (groove member). This "tongue-and-groove" interlocking system and method may be utilized in a wide range of patients with joint pathology to enhance healing and functional performance.

In another aspect of the present disclosure, a recipient site cutting guide for preparing a recipient site in tissue is described. The recipient site cutting guide comprises a height-determination (H-G) arm and a blade arm with a cutting slot, one or more guide holes, and one or more fixation holes. In one embodiment, the height-determination (H-G) arm and the blade arm are arranged so as to define an "L" shape. The configurations, dimensions, and orientations of the cutting slot, the guide hole(s), and the fixation hole(s) may be altered or varied such that the recipient site may be created according to any desired specifications, e.g., such that the recipient site and the groove/channel define a particular length, height, and/or width.

In certain embodiments, the cutting slot may be configured as an elongate cavity running horizontally, e.g., more than half-way, across the blade arm in parallel relation to the height-determination (H-G) arm.

In certain embodiments, the guide hole(s) may be located near an end of the cutting slot, and a bottom curve/edge of the guide hole(s) may be set lower than the cutting slot.

In certain embodiments, the fixation hole(s) may be located below the cutting slot (on an opposite side of the height-determination (H-G) arm).

During use of the recipient site cutting guide, the height-determination (H-G) arm is placed on a surface of a patient's articular cartilage such that the distance between the height-determination (H-G) arm and the cutting slot on the blade arm determines the height of recipient site to receive a harvested allograft implant.

Multiple cutting guides defining varying distances between the height-determination to (H-G) arm and the cutting slot may be employed to create recipient sites of varying heights to accommodate different grafting requirements.

In another aspect of the present disclosure, a method of preparing a recipient site, e.g., a patient's tibial plateau, for receipt of an allograft is disclosed (which may comprise bone and articular cartilage), with or without attached meniscus. The method includes: i) selecting a recipient site cutting guide with a desired distance being defined between a height-determination (H-G) arm and a cutting slot, ii) placing the height-determination (H-G) arm on a surface of the patient's articular cartilage, iii) securing the recipient site cutting guide by temporary fixation methods via one or more fixation holes; iv) making a shelf locating cut from anterior to posterior in a central aspect of the recipient bone; and v) cutting along the cutting slot to detach a portion of the recipient bone to be removed.

In another aspect of the invention, a method for preparing an allograft recipient site, e.g., a patient's tibial plateua, is described. The method includes: i) selecting a recipient site cutting guide comprising a H-G arm and a blade arm, which further comprises a cutting slot, one or more guide holes with a slot or other such opening, and one or more fixation holes, so that the height between the H-G arm and the cutting slot is compatible with the allograft to be implanted, ii) placing the H-G arm of the cutting guide on a surface of the patient's articular cartilage, iii) securing the cutting guide by temporary fixation methods via the fixation hole(s), iv) creating a channel from anterior to posterior by drilling (or forming a channel) through the guide hole(s), and v) removing a portion of the native tibial plateau by cutting along the cutting slot.

In another aspect of the present disclosure, a donor cutting guide is disclosed that is used to create an allograft implant (which may comprise bone and articular cartilage), with or without an attached meniscus, having a desired thickness and a bulging outward-curved ledge (tongue member) that is configured and dimensioned for positioning within the to groove/channel (groove member) created at the recipient site through use of the recipient site cutting guide.

In another aspect of the disclosure, a cutting guide is disclosed for use in a surgical procedure to removed damaged tissue from a patient and form a recipient site configured and dimensioned to receive a donor graft. The cutting guide includes a first arm configured and dimensioned for abutment with a section of the damages tissue to be removed, and a second arm connected to the first arm.

The second arm includes at least one slot that is configured and dimensioned to receive a first cutting implement, as well as at least one hole. The first arm and the at least one slot define a distance therebetween corresponding to a desired dimension of the recipient site, e.g., the height of the recipient site.

In certain embodiments, the first arm and the second arm may subtend an angle approximately equal to 90°.

The at least one hole includes a first hole that is configured and dimensioned to receive a second cutting implement. The first hole defines a periphery, and is positioned adjacent an end of the at least one slot.

In certain embodiments, a portion of the periphery defined by the first hole may be positioned below the at least one slot. Additionally, or alternatively, a portion of the periphery defined by the first hole may be positioned above the at least one slot.

In certain embodiments, the at least one slot and the first hole may be oriented such that a central axis defined by the at least one slot bisects the first hole.

In certain embodiments, the at least one hole may further include a second hole that is configured and dimensioned to receive a fixation member to secure the cutting guide in relation to the damaged tissue.

In certain embodiments, the at least one slot may be linear in configuration.

In certain embodiments, the at least one slot may include a first slot and a second slot. In such embodiments, the first arm and the first slot define a first distance therebetween, and the first arm and the second slot define a second distance therebetween greater than the first distance.

In another aspect of the disclosure, a surgical cutting guide is disclosed for use in forming a donor graft from donor tissue. The cutting guide includes a body defining a channel extending along a first axis that is configured and dimensioned to receive the donor tissue, and a shaping member that is secured to the body such that the shaping member is rotatable in relation to the body about a second axis.

The body of the cutting guide defines an upper shelf and a lower shelf positioned on opposite sides of the shaping member.

The shaping member includes at least one vane having a linear portion and a non-linear portion, and extends into the channel such that as the donor tissue is advanced through the channel, the at least one vane shapes the donor tissue so as to form the donor graft.

In certain embodiments, the shaping member may be secured to the body of the cutting guide such that the second axis is transverse, e.g., orthogonal, in relation to the first axis.

The linear portion and the non-linear portion of the at least one vane are configured and dimensioned such that the donor graft defines a planar section and a tongue member positioned adjacent the planar section such that the tongue member extends outwardly in relation to the planar section.

In certain embodiments, the non-linear portion of the at least one vane may define at least one recess.

The cutting guide further includes a sled movable in relation to the body of the cutting guide to facilitate movement of the donor tissue through the channel.

In certain embodiments, the sled may include a textured surface to increase friction between the sled and the donor tissue during movement of the donor tissue through the channel.

In another aspect of the disclosure, a surgical system is disclosed for use in: (i) forming a donor graft from donor tissue; and (ii) removing damaged tissue from a patient to form a recipient site configured and dimensioned to receive the donor graft. The system includes a first cutting guide configured and dimensioned to form the donor graft from the donor tissue, and a second cutting guide configured and dimensioned to facilitate formation of the recipient site.

The first cutting guide includes a body defining a channel that is configured and dimensioned to receive the donor tissue, and a shaping member that is secured to the body such that the shaping member is rotatable in relation to the body.

The shaping member includes at least one vane having a linear portion and a non-linear portion, and extends into the channel whereby as the donor tissue is advanced through the channel, the at least one vane shapes the donor tissue to form the donor graft to include a planar section and a tongue member that extends outwardly in relation to the planar section.

The second cutting guide includes a first arm that is configured and dimensioned for abutment with a section of the damaged tissue to be removed, and a second arm that is connected to the first arm. The second arm includes at least one slot that is configured and dimensioned to receive a first cutting implement so as to define a planar surface at the recipient tissue corresponding in configuration and dimensions to the planar section of the donor graft. The second arm also includes at least one hole that is configured and dimensioned to receive a second cutting implement so as to define a channel at the recipient site configured and dimensioned to receive the tongue member of the donor graft such that the recipient site receives the donor graft in an interlocking fashion.

In certain embodiments, the first arm and the second arm may subtend an angle of approximately 90°.

The at least one hole includes a first hole defining a periphery that is positioned adjacent an end of the at least one slot.

In certain embodiments, a portion of the periphery defined by the first hole is positioned below the at least one slot.

In certain embodiments, the at least one hole includes a second hole configured and dimensioned to receive a fixation member to secure the second cutting guide in relation to the damaged tissue.

The channel defined by the body of the first cutting guide extends along a first axis, and the shaping member is rotatable in relation to the body of the first cutting guide about a second axis. In certain embodiments, the shaping member may be secured to the body of the first cutting guide such that the second axis is transverse, e.g., orthogonal, in relation to the first axis.

The linear portion of the at least one vane is configured and dimensioned to shape the planar section of the donor graft, and the non-linear portion of the at least one vane is configured and dimensioned to shape the tongue member of the donor graft.

In certain embodiments, the non-linear portion of the at least one vane may define at least one recess.

In certain embodiments, the at least one recess may be curvate in configuration.

In another aspect of the disclosure, a method of performing a surgical procedure is disclosed that includes inserting donor tissue into a donor cutting guide, which may include bone and cartilage, as well as an attached meniscus, and advancing the donor tissue into to contact with a shaping member rotatably secured to a body of the donor cutting guide such that a vane of the shaping member shapes the donor tissue into a donor graft including a planar section and a tongue member that extends outwardly in relation to the planar section.

In certain embodiments, the method may further include harvesting the donor tissue from a donor site.

In certain embodiments, harvesting the donor tissue may include harvesting the donor tissue with an attached meniscus.

Inserting the donor tissue into the donor cutting guide includes positioning the donor tissue within a channel defined by the body of the donor cutting guide, and more specifically, on a lower shelf defined by the body of the donor cutting guide.

The disclosed method further includes advancing the donor tissue beyond the shaping member such that the donor tissue is positioned on an upper shelf defined by the body of the donor cutting guide after shaping into the donor graft.

Advancing the donor tissue includes repositioning a sled in contact with the donor tissue to thereby reposition the donor tissue.

Advancing the donor tissue into contact with the shaping member includes shaping a first portion of the donor tissue with a linear portion of the vane to thereby form the planar section of the donor graft, and shaping a second portion of the donor tissue with a non-linear portion of the vane to thereby form the tongue member of the donor graft.

In certain embodiments, shaping the second portion of the donor tissue may include shaping the donor tissue with a recess defined by the vane.

In certain embodiments, shaping the donor tissue with the recess may include contacting the donor tissue with an arcuate surface defined by the recess.

The method further includes removing damaged tissue from a patient to form a to recipient site configured and dimensioned to receive the donor graft in an interlocking fashion.

Forming the recipient site includes positioning a first arm of a recipient cutting guide in abutment with a section of the damaged tissue to be removed, and a second arm of the recipient cutting guide in abutment with a section of tissue that will not be removed.

In certain embodiments, forming the recipient site may further include securing the recipient cutting guide in relation to the damaged tissue, e.g., via attachment of a fixation member to the tissue that will not be removed through a hole in the recipient cutting guide.

Forming the recipient site further includes forming a channel configured and dimensioned to receive the tongue member of the donor graft, e.g., by passing a cutting implement through a hole in the recipient cutting guide.

Forming the recipient site further includes making a cut that intersects the channel so as to form a planar surface at the recipient site configured and dimensioned for engagement with the planar section of the donor graft, i.e., by passing a cutting implement through a slot extending through the second arm of the recipient cutting guide.

The method further includes positioning the donor graft such that the donor graft interlocks with the recipient site, e.g., such that the tongue member of the donor graft is positioned within the channel at the recipient site.

In certain embodiments, the method may further include securing the donor graft to the recipient site.

Other objects, features, and advantages of various illustrative embodiments of the present disclosure will become apparent with reference to the accompanying drawings, and the detailed description that follows.

BRIEF DESCRIPTION OF THE DRAWINGS

Various embodiments of the present disclosure are described herein with reference to the figures, wherein:

FIG. 3 is a side, elevational view of a donor graft following the removal of damaged tissue and formation of the recipient site;

FIG. 4 is a top, perspective view of the recipient site;

FIG. 5 is a side, elevational view illustrating placement of the donor graft at the recipient site;

FIG. 6 is a top, perspective view illustrating placement of the donor graft at the recipient site;

DETAILED DESCRIPTION

Figure 1:
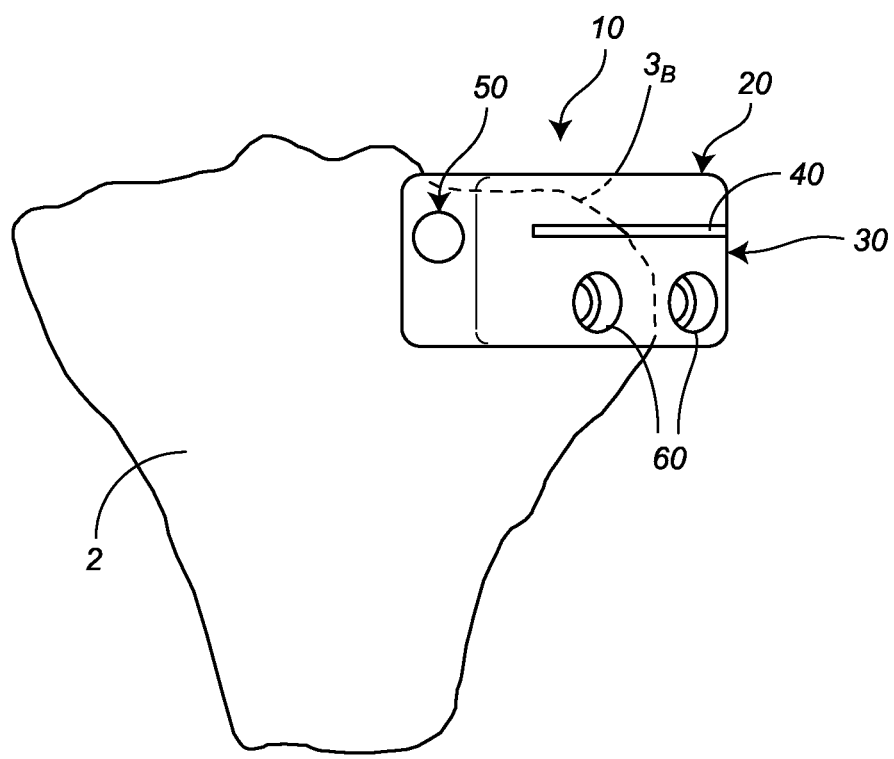
FIG. 1 is a front, elevational view illustrating a recipient cutting guide according to the principles of the present disclosure useful in the removal of damaged tissue, e.g., bone and cartilage, and the formation of a recipient site configured and dimensioned to receive a donor graft.
Figure 2:
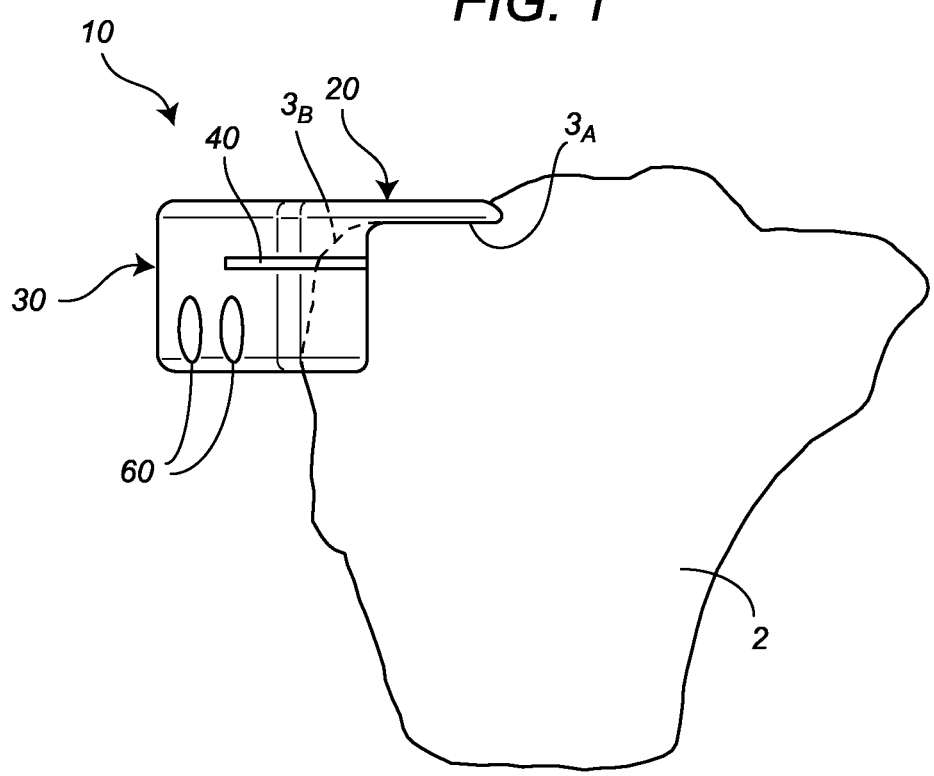
FIG. 2 is a side, elevational view of the presently disclosed recipient cutting guide.
Figure 7:
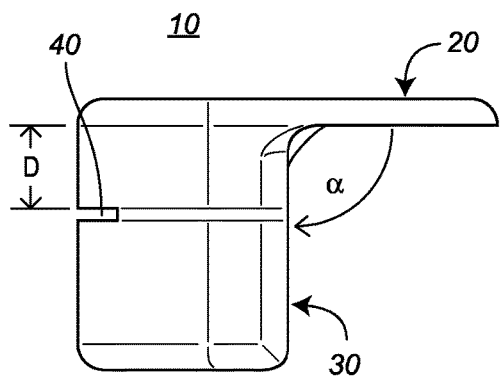
FIG. 7 is a side, elevational view of the presently disclosed recipient cutting guide.

In the following detailed description, reference is made to the accompanying drawings, which depict non-limiting, illustrative embodiments of the present disclosure. Throughout the present disclosure, the term "tissue" should be understood as including many forms of biological structural material, including, but not limited to, bone and cartilage. Additionally, the term "damaged tissue" should be understood to encompass any negatively affected tissue, including, but not limited to inflamed tissue, scarred tissue, and joint pathology. Additionally, the terms "height," "width," "thickness," "above," "below," "closer," "further," and any variation(s) thereof used herein are relative in character, and are intended to be interpreted in accordance with the perspective shown in the corresponding figure(s).

The present disclosure relates to apparatus, systems, and methods adapted for use in grafting procedures, e.g., tibial plateau allografting (with or without attached meniscus), and provides numerous benefits over known apparatus, systems, and methods. For example, the apparatus, systems, and methods disclosed allow for maintenance of the meniscus/bone junction, and facilitate transplantation of healthy cartilage and a healthy meniscus as a unit, as opposed to being transplanted separately. Moreover, the apparatus disclosed herein minimize the amount of native tissue that is removed to form the recipient site, while still allowing for appropriate fixation of the donor graft.

With reference now to FIGS. 1-12, a cutting guide 10 is illustrated for use during a surgical procedure in the preparation of a recipient site 5 (FIGS. 3-6) in tissue 2, e.g., a patient's tibial plateau, to receive a donor graft 1, e.g., a tibial plateau allograft, and the removal of damaged tissue.

The recipient site cutting guide 10 may include, e.g., be formed from, any material suitable for use in surgical practice, e.g., plastics, polymers, aluminum, stainless steel, titanium, and combinations thereof, and includes a generally horizontal first arm, e.g., a height-determination (H-G) arm, identified by the reference character 20, and a generally vertical second arm, e.g., a blade arm, identified by the reference character 30. In the illustrated embodiment, the arms 20, 30 are integrally, e.g., monolithically, formed. In alternate embodiments, however, other suitable methods of attachment may be employed to connect the arms 20, 30, e.g., one or more connectors or fasteners may be employed, or the arms 20, 30 may be welded together.

The arms 20, 30 are connected such that the cutting guide 10 defines a generally "L-shaped" configuration, e.g., such that the arms 20, 30 subtend a fixed angle α (FIG. 7) of approximately 90°, e.g., 60°-120°. In alternate embodiments, however, if necessary or desirable, the configuration of the cutting guide 10 may be varied to alter the angle α. For example, the arms 20, 30 may be arranged such that the angle α lies outside the range of 60°-120° dependent upon the requirements of a particular surgical procedure. Additionally, it is envisioned that the arms 20, 30 may movably connected to one another such that the angle α may be adjusted by the user on an as-needed basis, e.g., during the course of a surgical procedure.

The second arm 30 includes a cutting slot 40, one or more guide holes, 50, and one or more fixation holes 60. Although illustrated as including a single cutting slot 40, a single guide hole 50, and a pair of fixation holes 60 in the embodiment illustrated in FIGS. 7-12, the number of cutting slots 40, guide holes 50, and fixation holes 60 may be varied in alternate embodiments of the cutting guide 10 without departing from the scope of the present disclosure.

The cutting slot 40 extends horizontally across the second arm 30, and is configured and dimensioned to receive a cutting implement, e.g., a sagittal saw (not shown). In the illustrated embodiment, the cutting slot 40 and the first arm 20 are shown as extending in parallel relation, i.e., along non-intersecting axes. In alternate embodiments, however, the cutting slot 40 and the first arm 20 may be arranged so as to extend along intersecting axes. Additionally, while the cutting slot 40 is illustrated as being linear in configuration in the embodiment shown in FIGS. 7-12, in alternate embodiments, the cutting slot 40 may be non-linear in configuration. For example, the cutting slot 40 may include one or more arcuate and/or linear segments or sections.

The first arm 20 and the cutting slot 40 define a distance D (FIG. 7) therebetween that determines the vertical height (thickness) of the recipient site 5 (FIGS. 3-6), as discussed in further detail below. In general, the distance D will lie within the range of approximately 2 cm to approximately 20 cm (±25%). In most surgical applications, however, a distance D of approximately 6 cm to approximately 10 cm is standard.

Figure 8:
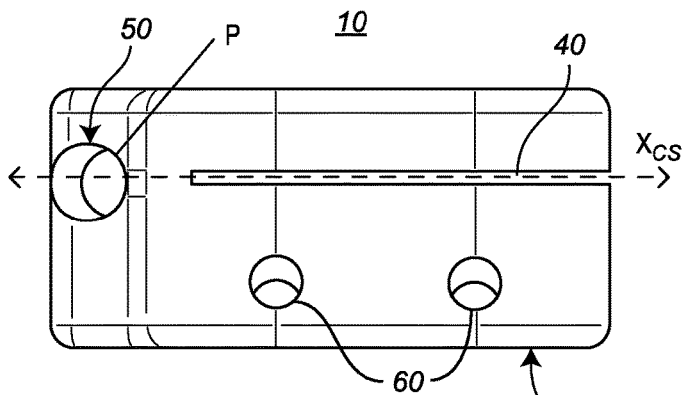
FIG. 8 is a front, elevational view of the presently disclosed recipient cutting guide.
Figure 9:
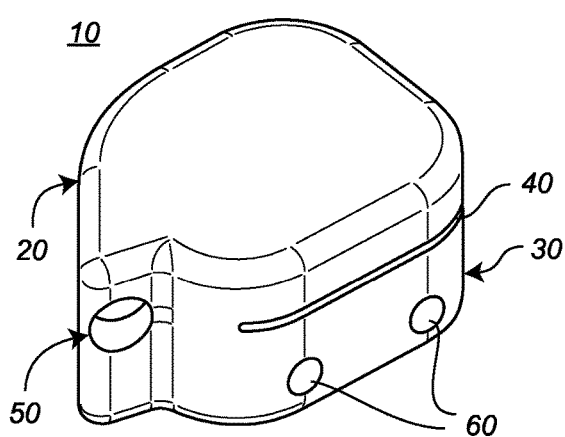
FIGS. 9 and 10 are top, perspective views of the presently disclosed recipient cutting guide.
Figure 10:
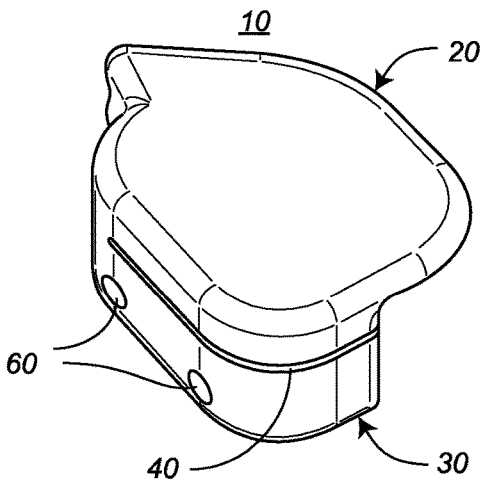
Figure 11:
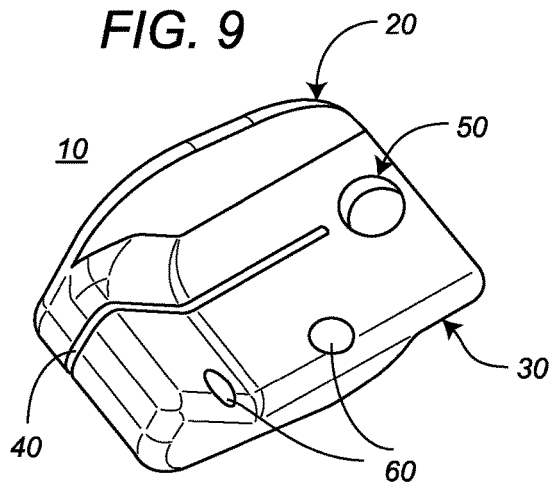
FIGS. 11 and 12 are bottom, perspective views of the presently disclosed recipient cutting guide.
Figure 12:
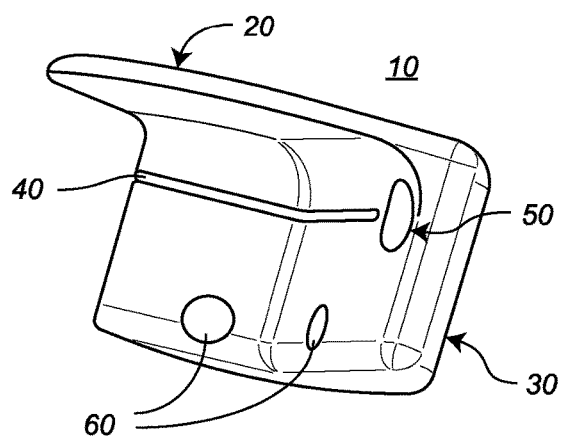

The guide hole 50 is located adjacent an end of the cutting slot 40, and defines a periphery P (FIG. 8). Although illustrated as being separated from the cutting slot 40, i.e., such that there is not communication between the guide hole 50 and the cutting slot 40, in alternate embodiments, the guide hole 50 and the cutting slot 40 may intersect. Additionally, while illustrated as circular in configuration in FIGS. 7-12, the guide hole 50 may define alternate configurations in other embodiments of the cutting guide 10, e.g., the guide hole 50 may be elliptical, ovoid, rectangular, etc.

As seen in FIG. 8, for example, the guide hole 50 and the cutting slot 40 are oriented such that an upper portion of the periphery P of the guide hole 50 is located above the cutting slot 40 (closer to the first arm 20), and a lower portion of the periphery P of the guide hole 50 is located below the cutting slot 40 (further from the first arm 20). For example, it is envisioned that a central axis $X_{CS}$ (FIG. 8) of the cutting slot 40 may bisect the guide hole 50.

With continued reference to FIGS. 7-12, the fixation holes 60 will be discussed. The fixation holes 60 are configured and dimensioned to removably receive fixation members (not shown), e.g., pins, screws, nails, or the like, which can be used to secure the cutting guide 10 to the tissue 2 (FIGS. 3-6), e.g., tibial bone, in which the recipient site 5 is formed, as discussed in further detail below. In the illustrated embodiment, the fixation holes 60 are located below the cutting slot 40. In alternate embodiments, however, the specific location of the fixation holes 60 may be altered or varied. For example, in one embodiment, it is envisioned that the fixation holes 60 may be located above the cutting slot 40, whereas in another embodiment, it is envisioned that the cutting guide 10 may include one fixation hole 60 located above the cutting slot 40, and another fixation hole 60 located below, or in line with, the cutting slot 40.

Although illustrated as being circular in configuration in the embodiment of the cutting guide 10 shown in FIGS. 7-12, the fixation holes 60 may define alternate configurations in other embodiments of the present disclosure. For example, the fixation holes 60 may be elliptical, ovoid, rectangular, etc.

With reference now to FIGS. 1-12, use of the recipient site cutting guide 10 will be discussed in connection with the removal of damaged tissue, and formation of the recipient site 5 (FIGS. 3-6) in preparation to receive a donor graft 1.

Initially, the recipient site cutting guide 10 is selected according to the requirements of the procedure, e.g., such that the dimensions defined by the recipient site 5 correspond to those of the donor graft 1, which may include an attached meniscus 4, as seen in FIGS. 3, 5, and 6. For example, the recipient site cutting guide 10 may be selected based upon the distance D (FIG. 7) defined between the first arm 20 and the cutting slot 40 such that the recipient site 5 is dimensioned to define a particular height in correspondence with the height (thickness) of the donor graft 1. The selected recipient site cutting guide 10 is then positioned such that the first arm 20 abuts a portion $3_A$ (FIG. 2) of the tissue 2 to be removed, i.e., damaged tissue, located above the cutting slot 40, and the second arm 30 abuts a portion $3_B$ of the tissue 2 that will not be removed, located below the cutting slot 40. The configuration and dimensions of the recipient site cutting guide 10, e.g., the location and dimensions of the cutting slot 40, are such that the amount of native tissue 2 removed to form the recipient site 5 is minimized, while still allowing for appropriate fixation of the donor graft 1.

After positioning the recipient site cutting guide 10, the cutting guide 10 is then secured to the tissue 2 by fixation members (not shown) inserted through the fixation holes 60. Alternatively, the user may simply apply pressure to the recipient site cutting guide 10 to hold the recipient site cutting guide 10 in place.

Thereafter, a drill bit (not shown), or other such cutting implement, is inserted into, and advanced through, the guide hole 50 into contact with the tissue 2 to create a channel 6 (FIGS. 3, 4), e.g., from anterior to posterior. A cut is then made along the cutting slot 40 using a saggital saw (not shown), or other such cutting implement, until the channel 6 is reached so as to define an upper surface 7 of the recipient site 5. For example, with reference to FIGS. 1-6 in particular, due to the linear configuration of the cutting slot 40 included in the cutting guide 10, the cut made in the tissue 2 results in a planar configuration at the upper surface 7 of the recipient site 5. In alternate embodiments, however, i.e., embodiments wherein the cuttings slot 40 is non-linear in configuration, the upper surface 7 of the recipient site 5 may be formed so as to define a non-planar, or otherwise irregular configuration.

After completion of the cut, the cutting implement is removed from the cutting slot 40, the fixation members (not shown) can be removed from the fixation holes 60, and the portion $3_A$ (FIG. 2) of the tissue 2 to be removed can be separated from the remainder of the tissue 2, revealing the recipient site 5, including the aforementioned channel 6 and upper surface 7.

Figure 13:
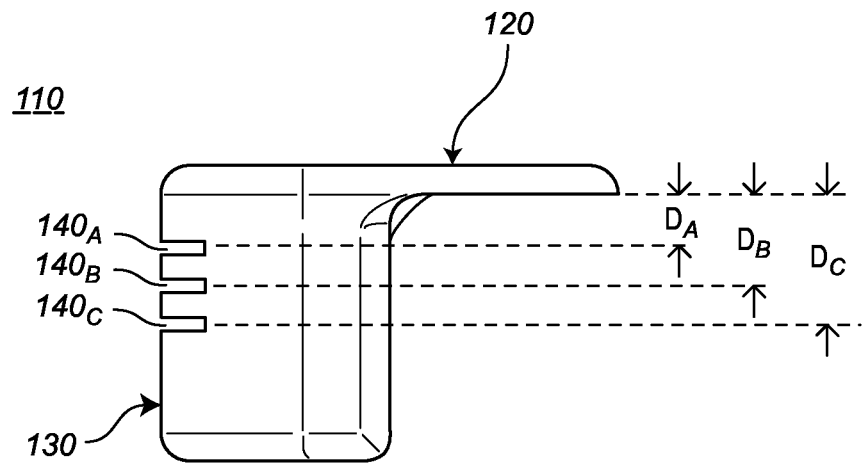
FIG. 13 is a side, elevational view of an alternate embodiment of the presently disclosed recipient cutting guide.
Figure 14:
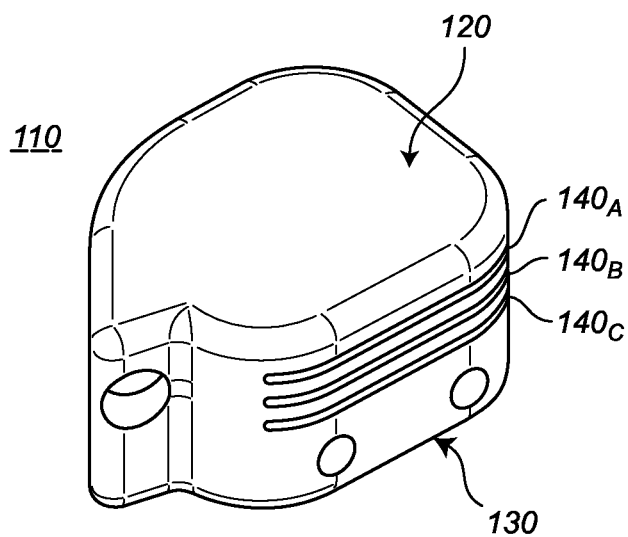
FIG. 14 is a top, perspective view of the recipient cutting guide shown in FIG. 13.

FIGS. 13 and 14 illustrate an alternate embodiment of the presently disclosed recipient site cutting guide, which is referred to generally by the reference character 110. The cutting guide 110 is identical to the cutting guide 10 discussed above in connection with FIGS. 7-12, for example, but for any distinctions that are specifically noted. Accordingly, a discussion of certain features common to the cutting guides 10, 110 may be omitted in the interest of brevity.

To increase versatility of the cutting guide 110, and the creation of recipient sites 5 (FIGS. 3-6) of various dimensions, e.g., heights, the cutting guide 110 includes a first arm 120, and a second arm 130 with a series of cutting slots 140, each of which is located a different distance from the first arm 120. For example, in the embodiment illustrated in FIGS. 13 and 14, the second arm 130 includes cutting slots $140_A$, $140_B$, $140_C$, wherein the first arm 120 is spaced a distance $D_A$ from the cutting slot $140_A$, a distance $D_B$ from the cutting slot $140_B$ greater than the distance $D_A$, and a distance $D_C$ from the cutting slot $140_C$ greater than the distance $D_B$.

The method of using the cutting guide 110 is identical to that of the cutting guide 10, but for the fact that the user has the ability to choose a specific cutting slot, e.g., one of the cutting slots $140_A$, $140_B$, $140_C$ in the embodiment shown in FIGS. 13 and 14, based upon the requirements of the particular procedure. For example, dependent upon the characteristics of the patient, and/or those of the damaged tissue to be removed, the user may elect to use one of the cutting slots $140_A$, $140_B$, $140_C$ as opposed to another to guide the cutting implement during formation of the upper surface 7 (FIGS. 3-7) of the recipient site 5.

In an alternate method of use, it is envisioned that more than one of the cutting slots $140_A$, $140_B$, $140_C$ may be employed during a surgical procedure. For example, an initial cut may be made using the cutting slot $140_A$, and thereafter, one ore more additional cuts may be made using the cutting slot $140_B$ and/or the cutting slot $140_C$ to allow for the progressive removal of the tissue and definition of the recipient site 5, e.g., to reduce patient trauma and/or inflammation at the recipient site 5.

With reference now to FIGS. 15-20, a donor implant cutting guide 200 will be discussed useful in formation of the aforementioned donor graft 1 (FIGS. 3-6, 15). The cutting guide 200 may include, e.g., be formed from, any material suitable for use in surgical practice, e.g., plastics, polymers, aluminum, stainless steel, titanium, and combinations thereof, and includes a body 202, a shaping member 204, and a movable sled 206.

The body 202 of the cutting guide 200 defines a channel 208 that is configured and dimensioned to receive donor tissue T, which may include an attached meniscus 4 (FIGS. 3, 5, 6, 15, 16). The channel 208 extends along an axis X, and is defined by sidewalls 210, 212, and respective lower and upper shelves 214, 216 positioned on opposite sides of the shaping member 204. The lower shelf 214 is spaced a first distance $D_1$ (FIG. 17) from a bottom wall 218 of the body 202, and the upper shelf 216 is spaced a second, greater distance $D_2$ from the bottom wall 218 of the body 202.

Although illustrated as extending in parallel relation to the bottom wall 218 of the body 202 in the embodiment illustrated in FIGS. 15-20, in alternate embodiments of the cutting guide 200, the shelf 214 and/or the shelf 216 may extend at an angle to the bottom wall 218 so as to either assist or resist movement of the donor tissue T through the channel 208. For example, either or both of the shelves 214, 216 may be angled toward the shaping member 204, or away from the shaping member 204.

The shaping member 204 resides within a well 220 defined by the body 202, and is secured to the body 202 such that the shaping member 204 is rotatable in relation to the body 202 about a fixed axis Y (FIG. 15) that extends in transverse relation to the axis X defined by the channel 208. For example, in the embodiment seen in FIG. 15, the shaping member 204 is oriented such that the axis Y is orthogonal in relation to the axis X. In alternate embodiments, however, the shaping member 204 may be oriented such that the axes X, Y subtend an angle other than 90°, e.g., 45°.

The shaping member 204 may be actuated, i.e., caused to rotate, by an automated mechanism, e.g., a motor (not shown), or alternatively, under manual power via the application of force by a user. For example, the shaping member 204 may be rotated by a crank (not shown) connected to the shaping member 204.

The shaping member 204 includes a drum 222, and one or more vanes 224. While the vanes 224 may include sharpened cutting edges 226 (FIGS. 18, 19), as illustrated in the embodiment seen in FIGS. 15-20, the vanes 224 may be devoid of any sharpened edges in alternate embodiments of the cutting guide 200. Additionally, while the shaping member 204 is illustrated as including four (4) vanes 224 in the embodiment of the cutting guide 200 shown in FIGS. 15-20, the number of vanes 224 may be increased or decreased in alternate embodiments of the cutting guide 200 without departing from the scope of the present to disclosure, e.g., to reduce manufacturing costs.

The vanes 224 extend outwardly from the drum 222 into the channel 208. Specifically, the shaping member 204 is positioned within the well 220 such that the edges 226 of the vanes 224 align with the upper shelf 216, i.e., such that the maximum linear separation realized between the vanes 224 and the bottom wall 218 of the body 202 during rotation of the shaping member 204 is equivalent to the distance $D_2$ (FIG. 17) defined between the upper shelf 216 and the bottom wall 218.

The vanes 224 are configured and dimensioned to shape the donor tissue T into the donor graft 1 (FIGS. 3, 5, 6) in correspondence with the configuration of the recipient site 5 (FIGS. 3-6). For example, in the embodiment of the cutting guide 200 illustrated in FIGS. 15-20, to facilitate shaping of the donor tissue T in the desired manner, the vanes 224 include a linear portion 228 (FIG. 19), and a non-linear portion 230 defining one or more recesses 232. In the specific embodiment shown, the vanes 224 are illustrated as including a single, curvate recess 232 defining an arcuate surface 234 that extends inwardly, toward the axis Y, resulting in a generally C-shaped configuration. In alternate embodiments, however, the recesses 232 may be present in greater number, and/or may define alternative configurations. For example, each vane 224 may include a pair of recesses 232 that are triangular in configuration.

Additionally, or alternatively, it is envisioned that the non-linear portion 230 of the vanes 224 may include one or more projections (not shown) extending outwardly, away from the axis Y.

Figure 15:
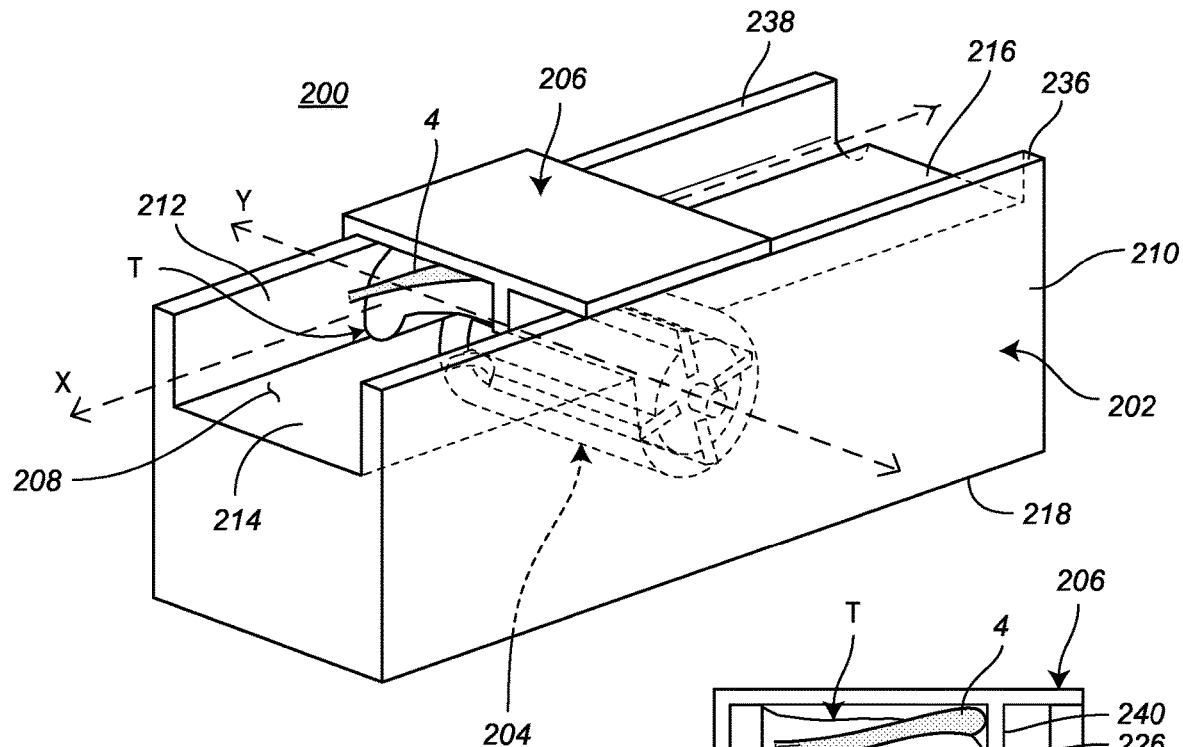
FIG. 15 is a top, perspective view of a donor cutting guide useful in forming the donor graft shown in FIG. 3 from donor tissue.
Figure 16:
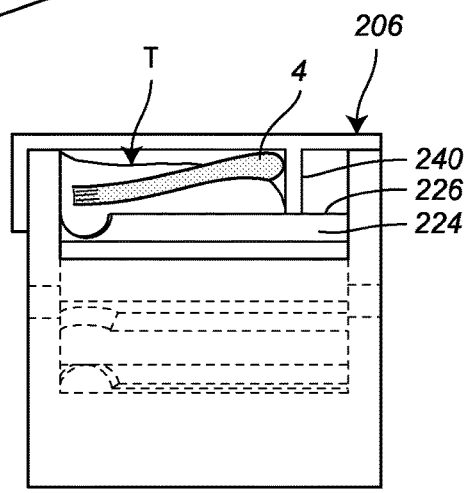
FIG. 16 is an end view of the presently disclosed donor cutting guide and the donor tissue.
Figure 17:
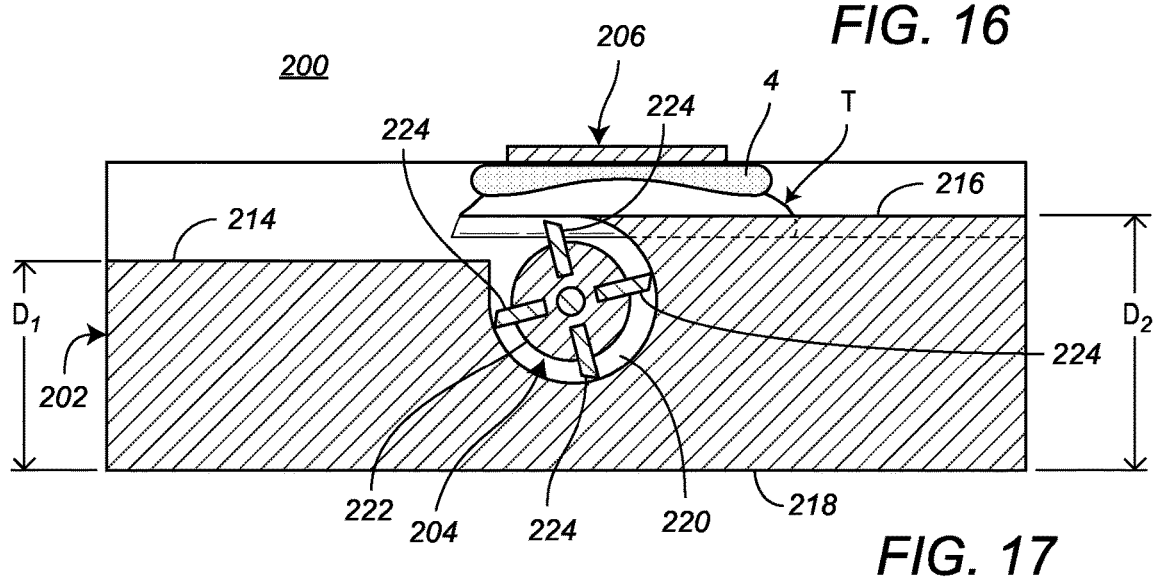
FIG. 17 is a longitudinal, cross-sectional view of the presently disclosed donor cutting guide and the donor tissue.
Figure 18:
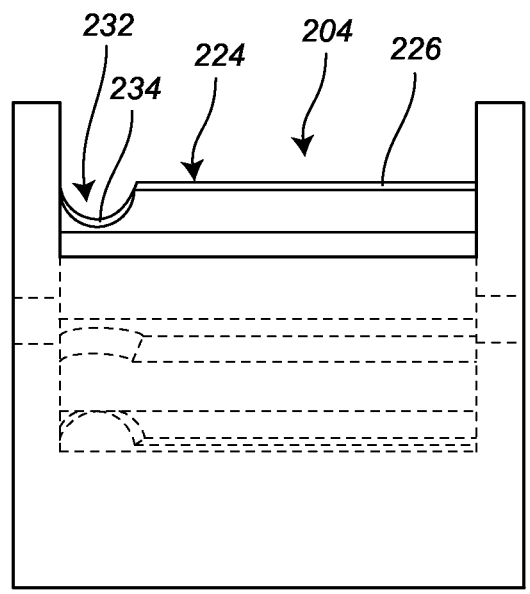
FIG. 18 is a partial, end view of the presently disclosed donor cutting guide.
Figure 19:
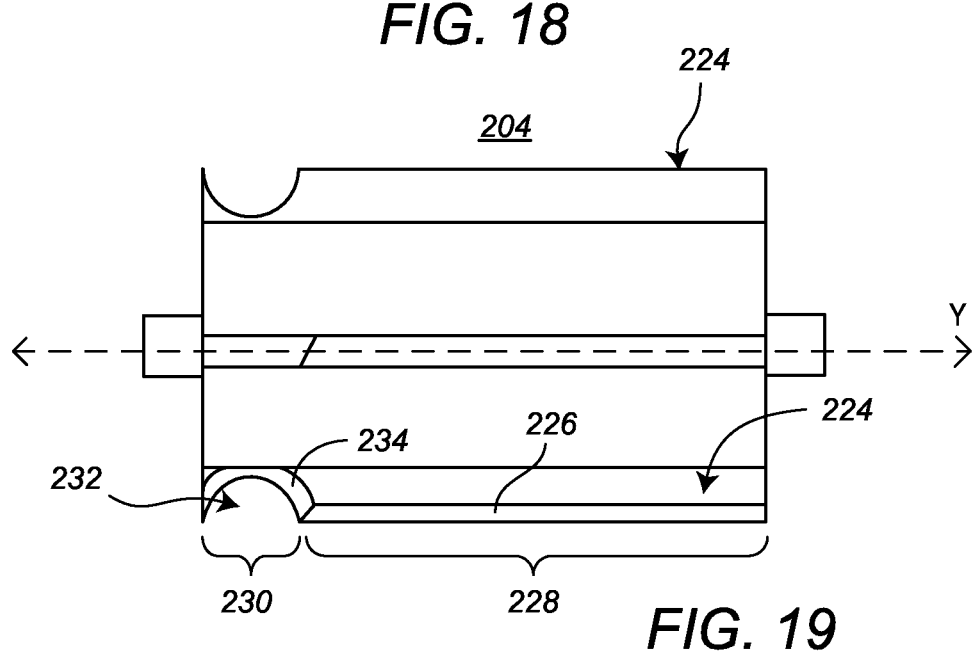
FIG. 19 is a side, elevational view illustrating a shaping member of the presently disclosed donor cutting guide.
Figure 20:
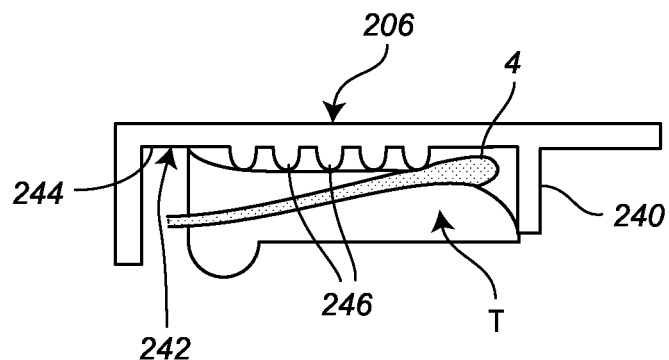
FIG. 20 is a partial, end view illustrating a sled of the presently disclosed donor cutting guide together with the donor tissue.

With reference now to FIGS. 15 and 20 in particular, the sled 206 will be discussed. During operation of the cutting guide 200, the sled 206 is used to stabilize and move the donor tissue T through the channel 208 across the lower shelf 214 into contact with the shaping member 204 and onto the upper shelf 216. To facilitate movement of the donor tissue T, the sled 206 is configured and dimensioned to slide in relation to the body 202 of the cutting guide 200, and may be either fixedly or removably connected thereto in any manner facilitating movement in this manner. For example, the sled 206 may rest upon upper surfaces 236, 238 (FIG. 15) defined by the sidewalls 210, 212 of the body 202 such that the sled 206 slides along the upper surfaces 236, 238 during movement.

In one embodiment, such as the embodiment shown in FIGS. 15 and 20, for example, the sled 206 includes a shoulder 240 that depends from an underside 242 (FIG. 20) thereof which may be used to urge the donor tissue T into contact with one of the sidewalls 210, 212 (FIG. 15) during movement of the donor tissue T through the channel 208 to further stabilize the donor tissue T, e.g., during shaping.

In one embodiment, seen in FIGS. 15 and 20 for example, the underside 242 of the sled 206 may include a textured surface 244 to increase friction between the sled 206 and the donor tissue T, and thus, control over the donor tissue T during movement through the channel 208. For example, the underside 242 of the sled 206 may include one or more protrusions 246 configured as detents, teeth, or the like. Alternatively, the underside 242 of the sled 206 may be non-textured.

Additionally, or alternatively, the sled 206 may include retaining structure (not shown), e.g., one or more pins, clamps, jaws, or the like, to secure the donor tissue T to the sled 206.

With reference now to FIGS. 3-6 and 15-20, use of the cutting guide 200 will be discussed in connection with formation of the aforementioned donor graft 1.

Initially, the donor tissue T is harvested from a larger section of tissue (not shown), e.g., through use of a saggital saw, scalpel etc., and is fed into the cutting guide 200. If necessary, the donor tissue T can be shaped or trimmed so as to fit within the confines of the channel 208 (FIG. 15) defined by the body 202 of the donor implant cutting guide 200. to Specifically, the donor tissue T is positioned on the lower shelf 214, and is stabilized using the sled 206, i.e., the donor tissue T is positioned between the lower shelf 214 and the sled 206. Using the sled 206, the donor tissue T is advanced into contact with the shaping member 204 whereby the vanes 224 remove portions of the donor tissue T in accordance with a pattern determined by the configuration and dimensions thereof. Specifically, in the illustrated embodiment, the linear portion 228 (FIG. 19) of the vanes 224 shape a section of the donor tissue T so as to define a planar section 8 (FIG. 3) that corresponds in configurations and dimensions to the upper surface 7 of the recipient site 5, while the non-linear portion 230 (FIG. 19) of the vanes 224 simultaneously shape an adjacent section of the donor tissue T so as to define a tongue member 9 (FIG. 3). The tongue member 9 corresponds in configurations and dimensions to the channel 6 defined by the recipient site 5, and extends transversely in relation to the length and width of the planar section 8 of the donor graft 1 such that the tongue member 9 extends outwardly in relation to the planar section 8.

As the donor tissue T passes by the shaping member 204, it is supported by the upper shelf 216. After shaping of the donor tissue T has been completed, i.e., when the donor graft 1 has been formed, the donor graft 1 is placed at the recipient site 5 (FIGS. 3-6). Specifically, the planar section 8 of the donor graft 1 is positioned in abutment with the upper surface 7 of the recipient site 5, and the tongue member 9 is positioned within the channel 6, as shown in FIGS. 3, 5 and 6, whereby the donor graft 1 and the recipient site 5 mate in an interlocking fashion so as to inhibit movement of the donor graft 1 in relation to the recipient site 5, e.g., motion in the medial-lateral direction.

In various embodiments of the present disclosure, the configurations, dimensions, and orientations of the cutting slot 40, the guide hole 50, and the fixation holes 60 of the cutting guide 10 (FIGS. 7-12) may be altered or varied, as can the configuration and dimensions of the vanes 224, the recesses 232, and the shelves 214, 216 of the cutting guide 200 (FIG. 15), so as to create a recipient site 5 (FIG. 3) and a donor graft 1 that interlock in any desired manner.

With reference again to FIG. 3, following placement of the donor graft 1, the donor graft 1 can be attached to the recipient site 5 using either temporary or permanent attachment structures (not shown), e.g., fixation screws, bone plates, or the like.

While the present disclosure has been described in connection with specific embodiments thereof, it will be understood that the subject matter of the present disclosure is capable of further modifications. For example, persons skilled in the art will understand that additional components and features may be added to any of the embodiments discussed herein above, and that those elements and features described in connection with any one embodiment may also be applicable to, or combined with, those of any other embodiment, without departing from the scope of the present disclosure.

The scope of the present disclosure is intended to cover any variations, uses, and/or adaptations of the presently disclosed subject matter in accordance with the principles of the present disclosure, including such departures from the present disclosure as come within known or customary practice within the art to which the present disclosure pertains, and as may be applied to the elements, components, and features set forth herein above.

The invention claimed is:

1. A surgical cutting guide for use in forming a donor cartilage graft from donor cartilage tissue, the cutting guide comprising:

a body defining a channel extending along a first axis, said channel located below a topmost surface of the body, the channel being configured and dimensioned to receive the donor tissue; and a shaping member secured to the body such that the shaping member is rotatable in relation to the body about a second axis, the shaping member including at least one vane extending into the channel such that as the donor tissue is advanced through the channel, the at least one vane shapes the donor tissue so as to form the donor graft.

2. The cutting guide of claim 1, wherein the shaping member is secured to the body of the cutting guide such that the second axis is transverse in relation to the first axis.

3. The cutting guide of claim 2, wherein the shaping member is secured to the body of the cutting guide such that the second axis is orthogonal in relation to the first axis.

4. The cutting guide of claim 1, wherein the body of the cutting guide defines an upper shelf and a lower shelf positioned on opposite sides of the shaping member.

5. The cutting guide of claim 1, wherein the at least one vane includes a linear portion and a non-linear portion.

6. The cutting guide of claim 5, wherein the linear portion and the non-linear portion of the at least one vane are configured and dimensioned such that the donor cartilage graft defines a planar section, and a tongue member extending outwardly in relation to the planar section.

7. The cutting guide of claim 6, wherein the non-linear portion of the at least one vane defines at least one recess.

8. The cutting guide of claim 1 further including a sled movable in relation to the body of the cutting guide to urge the donor cartilage tissue through the channel.

9. The cutting guide of claim 8, wherein the sled includes a textured surface to increase friction between the sled and the donor cartilage tissue during movement of the donor cartilage tissue through the channel.

* * * * *